(12) United States Patent
Villani et al.

(10) Patent No.: US 6,670,484 B2
(45) Date of Patent: Dec. 30, 2003

(54) PROCESS FOR THE PRODUCTION OF R(+) α-LIPOIC ACID

(75) Inventors: Flavio Villani, Parma (IT); Antonio Nardi, Paderno Dugnano (IT); Annibale Salvi, Milan (IT); Giovanna Falabella, Milan (IT)

(73) Assignee: Laboratorio Chimico Internazionale S.p.A. (IT)

( * ) Notice: Subject to any disclaimer, the term of this patent is extended or adjusted under 35 U.S.C. 154(b) by 0 days.

(21) Appl. No.: 10/398,892

(22) PCT Filed: Oct. 8, 2001

(86) PCT No.: PCT/EP01/11575

§ 371 (c)(1),
(2), (4) Date: Apr. 9, 2003

(87) PCT Pub. No.: WO02/30918

PCT Pub. Date: Apr. 18, 2002

(65) Prior Publication Data

US 2003/0187279 A1 Oct. 2, 2003

(30) Foreign Application Priority Data

Oct. 10, 2000 (IT) .................................. MI2000A02187

(51) Int. Cl.[7] ........................................... C07D 339/02
(52) U.S. Cl. ....................................................... 549/39
(58) Field of Search ........................................... 549/39

(56) References Cited

U.S. PATENT DOCUMENTS

| | | | |
|---|---|---|---|
| 5,281,722 A | | 1/1994 | Blaschke et al. |
| 5,621,117 A | | 4/1997 | Bethge et al. |
| 5,776,973 A | * | 7/1998 | Garnett ........................ 514/440 |
| 5,965,618 A | * | 10/1999 | Perricone .................... 514/558 |
| 6,013,663 A | * | 1/2000 | Fujita et al. ................. 514/440 |
| 6,441,024 B1 | * | 8/2002 | Klatt et al. .................. 514/440 |
| 6,462,202 B1 | * | 10/2002 | Schuhbauer et al. .......... 549/39 |

FOREIGN PATENT DOCUMENTS

| | | |
|---|---|---|
| EP | 0 702 953 A2 | 3/1996 |
| FR | 4 630 M | 6/1965 |

OTHER PUBLICATIONS

M. Pallavinci et al., "Synthesis of (R)–and (S)–Isopropylidene Glycerol," *Tetrahedron:Asymmetry*, 5:5–8 (1994).

* cited by examiner

*Primary Examiner*—Deborah C. Lambkin
(74) *Attorney, Agent, or Firm*—Nixon Peabody LLP

(57) ABSTRACT

Process for the synthesis of R(+)α-lipoic acid comprising the following stages: a) Salifying of racemic thioctic acid with R(+)α-methylbenzylamine; b) separation by filtration of the crystallized diastereoisomeric salt of R(+)α-lipoic acid-R(+)α-methylbenzylamine; c) purification by re-crystallization of the diastereoisomeric salt of R(+) α-lipoic acid-R(+)α-methylbenzylamine, in which the re-crystallization solvent consists of a mixture of non-polar/polar solvents; d) separation of the diastereoisomeric salt to obtain R(+)α-lipoic acid by reaction of said salt with acids selected from the group consisting of aliphatic hydroxycarboxylic acids having 3 to 6 carbon atoms and aqueous phosphoric acid.

28 Claims, No Drawings

PROCESS FOR THE PRODUCTION OF R(+) α-LIPOIC ACID

This Application is a 371 of PCT/EP01/11575 Oct. 08, 2001.

FIELD OF THE INVENTION

The present invention relates to a process of synthesis of R(+)α-lipoic acid through the formation of diastereoisomeric salts of racemic thioctic acid with optic isomers of α-methylbenzylamine.

STATE OF THE ART

It is well known from the state of the art about the process of resolution of racemic mixtures, or racemates, i.e. the splitting of a racemate into the enantiomers constituting it. The racemate is first transformed into a mixture of diastereoisomers by reaction with an optically active substance. The diastereoisomers thus obtained, characterized by different physical properties among which solubility, are generally separated by fractioned crystallization. The enantiomers of the starting racemic mixture are obtained from said separated diastereoisomers by simple chemical reactions of separation of said diastereoisomers.

U.S. Pat. No. 5,281,722 describes diastereoisomeric salts obtained from pure enatiomers of α-lipoic acid by reaction with optic isomers of α-methylbenzylamine. The state of the art describes methods for the preparation of said diastereoisomeric salts and their use as intermediate products in the resolution of a racemic mixture of thioctic acid in both optically active enantiomeric forms R(+) and S(−) of α-lipoic acid. The process of resolution of racemic thioctic acid has a low yield, in particular for the separation of the R(+)α-lipoic enantiomer (see Examples 7 and 8 of U.S. Pat. No. 5,281,722).

As a matter of fact, the purification processes described at the state of the art for diastereoisomeric salts have a low enantiomeric enrichment of the salt of the R(+)α-lipoic isomer. This is further confirmed by the high number of re-crystallizations carried out on diastereoisomeric salts before the scission reaction with acids.

Tests carried out by the Applicant show that the scission of the purified diastereoisomeric salts by addition of inorganic acids, for instance mineral acids such as 1N hydrochloric acid, to obtain the two separated optically active enantiomeric forms R(+) and S(−) of α-lipoic acid, as described in U.S. Pat. No. 5,281,722, results in low-quality enantiomers of α-lipoic acid presence of polymers).

The state of the art described the use of diastereoisomeric salts obtained from the enantiomers of α-lipoic acid by means of reaction with optically active bases in order to separate the isomers R(+) and S(−) of α-lipoic acid. However, the processes described at the state of the art, as verified by the Applicant, are characterized by complex and long methods for purifying intermediate diastereoisomeric salts, with low yields of resolution of racemates as well as an unsatisfying quality of the optic isomers thus obtained.

There was therefore a need for a process of synthesis of the optic isomer R(+) of α-lipoic acid starting from racemic thioctic acid with a higher resolution yield. Said process should consist of few stages of purification of intermediate diastereoisomeric salts, so as to obtain a R(+)α-lipoic acid of higher quality.

SUMMARY

It has now been found a new process of synthesis of R(+)α-lipoic acid through the resolution of racemic thioctic acid, said process to overcoming the disadvantages characterizing the processes at the state of the art, such as complexity, low yield and low quality of the optic isomers obtained.

Quite unexpectedly and surprisingly, the Applicant has found a new process of synthesis of R(+)α-lipoic acid by reacting racemic thioctic acid with the optically active base R(+)α-methylbenzylamine, thus obtaining the diastereoisomeric salt of R(+)α-lipoic acid-R(+)α-methylbenzylamine, followed by its purification by fractioned crystallization and scission of the salt with acids.

DETAILED DESCRIPTION OF THE INVENTION

An object of the present invention is therefore a process of synthesis of R(+)α-lipoic acid comprising the following stages:

a) salifying of racemic thioctic acid with R(+)α-methylbenzylamine (FEA), wherein the molar ratio FEA/racemic thioctic acid is between 0.45 and 0.70;

b) separation by filtration of the crystallized diastereoisomeric salt of R(+)α-lipoic acid-R(+)α-methylbenzylamine;

c) purification by re-crystallization of the diastereoisomeric salt of R(+)α-lipoic acid-R(+)α-methylbenzylamine, wherein the re-crystallization solvent consists of a mixture of non-polar/polar solvents, the polar solvent being maximum 20% by volume of the mixture, and the temperature of dissolution of the salt is between 50 and 75° C.;

d) separation of the diastereoisomeric salt to obtain R(+) α-lipoic acid by reaction of said salt with acids selected from the group consisting of aliphatic hydroxycarboxylic acids having 3 to 6 carbon atoms and aqueous phosphoric acid with a dilution between 2 and 10% by weight.

According to the process of synthesis of the present invention, in the salifying stage a) the molar ratio FEA/racemic thioctic acid is preferably between 0.55 and 0.65, still more preferably between 0.57 and 0.63. The salifying in stage a) is carried out at atmospheric pressure in an organic solvent, preferably toluene, at a temperature between 30 and 60° C., preferably between 35 and 40° C. The concentration of the racemic thioctic acid in salifying stage a) is between 5 and 40% w/v, preferably between 8 and 20% w/v, still more preferably between 9 and 13% w/v of solvent.

Stage b), i.e. separation by filtration of the diastereoisomeric salt, takes place at a temperature of 10 to 30° C., preferably at 25° C.

In stage c), i.e. purification by re-crystallization of the diastereoisomeric salts of R(+)α-lipoic acid-R(+)α-methylbenzylamine, the mixture of non-polar/polar solvents is preferably chosen between toluene/methanol and toluene/dimethylformamide (DMF). As far as the mixture toluene/methanol is concerned, the volume ratio of the solvents is between 80:20 and 99:1, preferably between 90:10 and 98.5:1.5, still more preferably between 91:9 and 98:2. As far as the mixture toluene/dimethylformamide (DMF) is concerned, the volume ratio of the solvents is between 70:30 and 85:15, preferably between 75:25 and 84:16, still more preferably 78:22 and 80:20. The concentration of the diastereoisomeric salt in purification stage c) is between 7 and 15% w/v, preferably between 9 and 14% w/v, still more preferably between 10 and 12% w/v of mixture of non-polar/polar solvents.

In stage c), i.e. purification of the diastereoisomeric salt, the dissolution of the latter, at a temperature preferably between 57 and 72° C., still more preferably between 60 and 70° C., is followed by the precipitation of the crystals of the salt of R(+)α-lipoic acid-R(+)α-methylbenzylamine by cooling at a temperature between 10 and 25° C.

In stage d), i.e. separation of the diastereoisomeric salt, the preferred aqueous phosphoric acid has a dilution between 4 and 8% by weight, still more preferred is phosphoric acid diluted at 5% by weight. In stage d), i.e. separation of the diastereoisomeric salt, the preferred hydroxy-carboxylic acid is citric acid in an equimolar amount with respect to the diastereoisomeric salt.

The yield of the process of synthesis of R(+)α-lipoic acid according to the present invention can be further increased through a stage d') providing for the recycling of the mother liquors from stage b), i.e. re-crystallization of the diastereoisomeric salt, and from stage c), i.e. purification of said salt by re-crystallization. Said stage d') of recycling of mother liquors comprises:

I. gathering of mother liquors from stages b) and c);
II. their treatment with acid aqueous solutions;
III. concentration to dryness of the organic phase by evaporation under vacuum, thus obtaining α-lipoic acid with an excess of the enantiomer S(−);
IV. racemization of α-lipoic acid with an excess of the enantiomer S(−) in an organic solvent having a boiling point above 200° C. and selected from the group consisting of: linear or branched aliphatic $C_{12}$–$C_{20}$ hydrocarbons, aromatic $C_{12}$–$C_{20}$ hydrocarbons, $C_{12}$–$C_{20}$ arylalkyl hydrocarbons or their mixtures, wherein the concentration of α-lipoic acid with an excess of the enantiomer S(−) is between 20% and 50% w/v of solvent, by heating at atmospheric pressure at a temperature between 170 and 210° C. for less than 10 hours;
V. recycling of racemic α-lipoic acid to reaction stage a).

In the stage of racemization of α-lipoic acid according to the present invention the organic solvent is preferably a solvent with a boiling point above 220° C., selected from the group consisting of mixtures of isomers of benzyltoluene (MARLOTHERM® LH), mixtures of partially hydrogenated terphenyls (DOWTHERM®, SANTOTHERM® 66), mixtures of alkylbenzenes (SANTOTHERM® 55), mixtures of diphenyl (DIPHYL®) and mixtures of diphenyl oxide (DIPHYL® DT). Still more preferred as solvent in the stage of racemization of α-lipoic acid is MARLOTHERM® LH, a mixture of isomers of benzyltoluene having a boiling point at atmospheric pressure between 278 and 282° C. The concentration of α-lipoic with an excess of the enantiomer S(−) in the racemization stage is preferably between 25% and 40% w/v, still more preferably between 30 and 35% w/v of solvent. The racemization temperature according to the present invention is preferably between 175 and 205° C., still more preferably between 180 and 200° C.

The following are some examples disclosing though not limiting the framework of the present invention.

EXAMPLE 1

36 g (0.174 moles) of racemic α-lipoic acid are dissolved in 360 ml of toluene at 38–39° C. This solution is added with 13.5 g (0.11 moles) of R(+)α-methylbenzylamine (FEA). The salt precipitates and is cooled down at 25° C. The solid is filtered, washed with 20 ml of toluene and then dried, thus obtaining 29 g of product. The salt is first crystallized with 250 ml of toluene and 5 ml of methanol, the mixture thus obtained is heated until dissolution (68–69° C.), then cooled down at 10° C. and filtered. The solid is washed with 15 ml of toluene and then dried, thus obtaining 25.9 g of product. The salt thus obtained is crystallized a second time with 200 ml of toluene and 6 ml of methanol. The mixture thus obtained is heated until dissolution (68° C.), then cooled down at 10° C. and filtered. The solid is washed with 10 ml of toluene and dried, thus obtaining 20.5 g of product. The latter is further re-crystallized with 160 ml of toluene and 7 ml of methanol. After dissolution (69–70° C.) it is cooled down at 10° C. and filtered. The solid is washed with 10 ml of toluene and dried, thus obtaining 18.2 g of product.

The diastereoisomeric salt (R(+)α-lipoic acid-R(+)α-methylbenzylamine) thus recrystallized is suspended in 120 ml of toluene at 36–37° C. A solution of citric acid (10.5 g) in methanol (21 ml) is dropped under stirring in 45 minutes and the whole is cooled down. During the cooling stage the citrate of R(+)α-methylbenzylamine precipitates and is removed by filtration and washed with 20 ml of toluene. The organic phases are united and concentrated under vacuum. The obtained residue is taken up with 75 ml of cyclohexane and 5 ml of ethyl acetate. The whole is heated at 39–40° C. and filtered on carbon. The clear solution thus obtained is cooled down at 7° C. (at 25–30° C. R(+)α-lipoic acid crystallizes), the solid obtained is filtered and washed with 10 ml of cyclohexane. The whole is dried, thus obtaining 9.9 g of R(+)α-lipoic acid (yield=55.0%).

$[\alpha]_d$=119.2 (c=1, ethanol); e.e. >99% (HPLC).

EXAMPLE 2

The mother liquors obtained from the re-crystallization of the salt of R(+)α-lipoic acid-R(+)α-methylbenzylamine resulting from Example 1 are gathered and extracted with 1 liter of 10% aqueous sulfuric acid and then washed twice with 100 ml of water. The whole is concentrated to dryness by evaporation under vacuum of toluene, thus obtaining 25 g of residual, i.e. recovered α-lipoic acid mainly containing the enantiomer S(−): enantiomeric excess=40% (chiral HPLC).

EXAMPLE 3

10 g (0.048 moles) of recovered α-lipoic acid having an enantiomeric excess of 40% (70% of S(−)α-lipoic acid+30% of R(+)α-lipoic acid) are suspended in 15 ml of Marlotherm® LH. The whole is heated at 180–182° C. for 5 hours under nitrogen atmosphere at a pressure of one atmosphere. The whole is then cooled down at 90° C., added with cyclohexane (70 ml) and treated with decolorizing carbon. The clear solution obtained is hot-filtered and then cooled down first for 5 hours at 25° C., and then for 1 hour at 6–8° C. The solid obtained is filtered, washed with cyclohexane and dried under vacuum, thus obtaining 8.1 g of racemic α-lipoic acid (yield=81%).

A second yield can be obtained from the mother liquors after concentration under vacuum, or alternatively cyclohexane can be removed by distillation and the remaining solution in Marlotherm® LH can be used for a second racemization.

$[\alpha]^{20}_d$=−1.6 enantiomer R(+)=49.4% (chiral HPLC).

EXAMPLE 4

20 g of S(−)α-lipoic acid are suspended in 30 ml of Marlotherm® LH. The suspension is heated at 194–196° C. for 7 hours under nitrogen atmosphere at a pressure of one atmosphere. The whole is cooled down at 90° C., added with cyclohexane (140 ml) and treated with decolorizing carbon. The clear solution obtained is hot-filtered and cooled down first for 5 hours at 25° C. and then for 1 hour at 6–8° C. The solid obtained is filtered, washed with cyclohexane and dried under vacuum, thus obtaining 16.5 g of racemic α-lipoic acid (yield=82.5%).

A second yield can be obtained from the mother liquors after concentration under vacuum, or alternatively cyclohexane can be removed by distillation and the remaining solution in Marlotherm® LH can be used for a second racemization.

$[\alpha]^{20}{}_d=-1.5$ enantiomer R(+)=49.5% (chiral HPLC)

COMPARATIVE EXAMPLE 5

36 g (0.174 moles) of racemic α-lipoic acid are dissolved in 360 ml of toluene at 38–39° C. This solution is added with 16.8 g (0.139 moles) of R(+)α-methylbenzylamine (FEA) with a molar ratio FEA/racemic thioctic acid=0.8. The salt precipitates and is cooled down at 25° C. The solid is filtered, washed with 20 ml of toluene and then dried, thus obtaining 41 g of product. Said product has a low enantiomeric enrichment of the salt of the R(+)α-lipoic: $[\alpha]^{20}{}_d=$ 13.6 (c=1, ethanol) with e.e.=18.3% (HPLC). Said product is re-crystallized five times giving 17.0 g of diastereoisomeric salt (R(+)α-lipoic acid-R(+)α-methylbenzylamine) with an optical purity of 85%.

COMPARATIVE EXAMPLE 6

50 g of salt of racemic α-lipoic acid with R(+)α-methylbenzylamine (FEA) resulting from stage b) of separation by filtration, according to Example 1, are added to a mixture consisting of 400 ml of toluene and 140 ml of methanol. The mixture thus obtained is heated until dissolution (45° C.), than cooled down at 22° C. No precipitation is observed. The mixture is further cooled down at 10° C. for 1 hour adding crystal seeds. No precipitation is observed. At the end, the mixture is cooled down at 6° C. for 1 hour adding again crystal seeds. No precipitation is observed.

COMPARATIVE EXAMPLE 7

83 g of re-crystallized diastereoisomeric salt R(+)α-lipoic acid-R(+) α-methylbenzylamine, resulting from the purification stage c) according to Example 1, are added under stirring to 414 ml of toluene. 21 ml of sulphuric acid, 50% by weight, are dropped under stirring in 30 minutes. The final pH at room temperature is 3.2. The organic phase is separate and washed first with 125 ml of water, afterwards with a 125 ml of an aqueous solution of sodium chloride at 10% by weight. The organic phase is de-hydrated on sodium sulfate and concentrate to dryness under vacuum by solvent evaporation. The obtained residue is taken up with 330 ml of cyclohexane and 22 ml of ethyl acetate. The whole is heated at 33° C. and filtered on carbon. The solution thus obtained is cooled down at 6°–7° C., the solid obtained is filtered and washed with 40 ml of cyclohexane. The whole is dried, thus obtaining 38.5 g of R(+)α-lipoic acid (yield=40.0%).

$[\alpha]_d=112$ (c=1, ethanol).

The scission of the purified diastereoisomeric salts by addition of inorganic acid, such as sulphuric acid, results in low-yield and low-quality enantiomers of α-lipoic acid.

Cromatographic Conditions for Determining the Enantiomeric Excess

Chromatographic column: chiral AGP column, size 100 mm×4 mm, with pre-column;
Mobile phase: 1 liter of 0.01 M solution of $Na_2HPO_4$, brought to pH=5 with diluted phosphoric acid, mixed with 150 ml of methanol.
Flow speed: 0.4 ml/minute
Pressure: 35 bar
Temperature: 20° C.
Wave length (α): 220 nm
Sample: 1.5–2 mg of substance dissolved in 20 ml of mobile phase.

What is claimed is:

1. Process for the synthesis of R(+)α-lipoic acid comprising the following stages:
    a) salifying of racemic thioctic acid with R(+)α-methylbenzylamine (FEA), wherein the molar ratio FEA/racemic thioctic acid is between 0.45 and 0.70;
    b) separation by filtration of the crystallized diastereoisomeric salt of R(+)α-lipoic acid-R(+)α-methylbenzylamine;
    c) purification by re-crystallization of the diastereoisomeric salt of R(+)α-lipoic acid-R(+)α-methylbenzylamine, wherein the re-crystallization solvent consists of a mixture of non-polar/polar solvents, the polar solvent being maximum 20% by volume of the mixture, and the temperature of dissolution of the salt is between 50 and 75° C.;
    d) separation of the diastereoisomeric salt to obtain R(+) α-lipoic acid by reaction of said salt with acids selected from the group consisting of aliphatic hydroxy carboxylic acids having 3 to 6 carbon atoms and aqueous phosphoric acid with a dilution between 2 and 10% by weight.

2. Process according to claim 1, wherein the molar ratio FEA/racemic thioctic acid is between 0.55 and 0.65.

3. Process according to claim 2, wherein the molar ratio FEA/racemic thioctic acid is between 0.57 and 0.63.

4. Process according to claim 1, wherein the concentration of racemic thioctic acid in salifying stage a) is between 5 and 40% w/v of solvent.

5. Process according to claim 4, wherein the concentration of racemic thioctic acid is between 8 and 20% w/v of solvent.

6. Process according to claim 5, wherein the concentration of racemic thioctic acid is between 9 and 13% w/v of solvent.

7. Process according to claim 1, wherein the mixture of non-polar/polar solvents is a mixture selected from the group consisting of toluene/methanol and toluene/dimethylformamide (DMF).

8. Process according to claim 7, wherein as far as the mixture toluene/methanol is concerned the volume ratio of the solvents is between 80:20 and 99:1.

9. Process according to claim 8, wherein the volume ratio toluene/methanol is between 90:10 and 98.5:1.5.

10. Process according to claim 9, wherein the volume ratio toluene/methanol is between 91:9 and 98:2.

11. Process according to claim 7, wherein as far as the mixture toluene/dimethylformamide (DMF) is concerned the volume ratio of the solvents is between 70:30 and 85:15.

12. Process according to claim 11, wherein the volume ratio toluene/dimethylformamide is between 75:25 and 84:16.

13. Process according to claim 12, wherein the volume ratio toluene/dimethylformamide is between 78:22 and 80:20.

14. Process according to claim 1, wherein the concentration of the diastereoisomeric salt in purification stage c) is between 7 and 15% w/v of mixture of non-polar/polar solvents.

15. Process according to claim 14, wherein the concentration of the salt is between 9 and 14% w/v of mixture of non-polar/polar solvents.

16. Process according to claim 15, wherein the concentration of the salt is between 10 and 12% w/v of mixture of non-polar/polar solvents.

17. Process according to claim 1, wherein in stage c), i.e. purification of the diastereoisomeric salt, the dissolution temperature is between 57 and 72° C.

18. Process according to claim 17, wherein the dissolution temperature is between 60 and 70° C.

19. Process according to claim 1, wherein in stage d) the acid is aqueous phosphoric acid with a dilution between 4 and 8% by weight.

20. Process according to claim 19, wherein the acid is phosphoric acid diluted at 5% by weight.

21. Process according to claim 1, wherein in stage d) the hydroxy-carboxylic acid is citric acid in an equimolar amount with respect to the diastereoisomeric salt.

22. Process according to claim 1, comprising a stage d') providing for the recycling of mother liquors, wherein said recycling stage d') comprises:

I. gathering of mother liquors from stages b) and c);

II. their treatment with acid aqueous solutions;

III. concentration to dryness of the organic phase by evaporation under vacuum, thus obtaining α-lipoic acid with an excess of the enantiomer S(−);

IV. racemization of α-lipoic acid with an excess of the enantiomer S(−) in an organic solvent having a boiling point above 200° C. and selected from the group consisting of: linear or branched aliphatic $C_{12}$–$C_{20}$ hydrocarbons, aromatic $C_{12}$–$C_{20}$ hydrocarbons, $C_{12}$–$C_{20}$ arylalkyl hydrocarbons or their mixtures, in which the concentration of α-lipoic acid with an excess of the enantiomer S(−) is between 20% and 50% w/v of solvent, by heating at atmospheric pressure at a temperature between 170 and 210° C. for less than 10 hours;

V. recycling of racemic α-lipoic acid of reaction stage a).

23. Process according to claim 22, wherein in the stage providing for the racemization of α-lipoic acid the solvent has a boiling point above 220° C. and is selected from the group consisting of mixtures of isomers of benzyltoluene (MARLOTHERM® LH), mixtures of partially hydrogenated terphenyls (DOWTHERM®, SANTOTHERME® 66), mixtures of alkylbenzenes (SANTOTHERM® 55), mixtures of diphenyl (DIPHYL®) and mixtures of diphenyl oxide (DIPHYL® DT).

24. Process according to claim 23, wherein the solvent is MARLOTHERM® LH, a mixture of isomers of benzyltoluene having a boiling point at atmospheric pressure between 278 and 282° C.

25. Process according to claim 22, wherein the concentration of α-lipoic acid with an excess of the enantiomer S(−) in the stage of racemization is preferably between 25% and 40% w/v of solvent.

26. Process according to claim 25, wherein the concentration of α-lipoic acid with an excess of the enantiomer S(−) is between 30% and 35% w/v of solvent.

27. Process according to claim 22, wherein the racemization temperature is between 175 and 205° C.

28. Process according to claim 27, wherein said temperature is between 180 and 200° C.

* * * * *